US008920519B2

(12) United States Patent  (10) Patent No.: US 8,920,519 B2
Johannes et al.  (45) Date of Patent: Dec. 30, 2014

(54) MULTIPLE GRASP PROSTHETIC TERMINAL DEVICE

(71) Applicant: The Johns Hopkins University, Baltimore, MD (US)

(72) Inventors: Matthew S. Johannes, Catonsville, MD (US); Robert S. Armiger, Catonsville, MD (US); Jonathan Kuniholm, Durham, NC (US)

(73) Assignee: The Johns Hopkins University, Baltimore, MD (US)

( * ) Notice: Subject to any disclaimer, the term of this patent is extended or adjusted under 35 U.S.C. 154(b) by 7 days.

(21) Appl. No.: 13/756,664

(22) Filed: Feb. 1, 2013

(65) Prior Publication Data

US 2013/0197671 A1  Aug. 1, 2013

Related U.S. Application Data

(60) Provisional application No. 61/593,523, filed on Feb. 1, 2012.

(51) Int. Cl.
*A61F 2/58* (2006.01)
*A61F 2/72* (2006.01)
*A61F 2/74* (2006.01)

(52) U.S. Cl.
CPC ............... *A61F 2/585* (2013.01); *A61F 2/586* (2013.01); *A61F 2/583* (2013.01); *A61F 2/72* (2013.01); *A61F 2002/587* (2013.01); *A61F 2002/741* (2013.01)
USPC .......................................................... 623/64

(58) Field of Classification Search
USPC .................... 623/57, 61, 62, 63, 64
See application file for complete search history.

(56) References Cited

U.S. PATENT DOCUMENTS

| | | | | |
|---|---|---|---|---|
| 2,844,236 | A | * | 7/1958 | Cole, Jr. ..................... 192/223.2 |
| 4,156,945 | A | * | 6/1979 | May ................................ 623/61 |
| 4,284,374 | A | * | 8/1981 | Senzaki ........................ 408/139 |
| 4,599,019 | A | * | 7/1986 | Ueberall ........................ 408/139 |
| 4,792,338 | A | * | 12/1988 | Rennerfelt ...................... 623/64 |
| 4,865,613 | A | * | 9/1989 | Rizzo .............................. 623/65 |
| 4,901,836 | A | * | 2/1990 | Stenmark et al. ........... 192/56.5 |
| 4,990,162 | A | * | 2/1991 | LeBlanc et al. ................. 623/63 |
| 5,888,246 | A | * | 3/1999 | Gow ............................... 623/64 |
| 7,828,857 | B2 | * | 11/2010 | Farnsworth et al. ............ 623/64 |
| 8,052,761 | B2 | * | 11/2011 | Veatch ............................ 623/64 |
| 8,231,158 | B2 | | 7/2012 | Dollar et al. |

(Continued)

FOREIGN PATENT DOCUMENTS

| WO | 2005065264 | 7/2005 |
|---|---|---|
| WO | 2012071343 | 5/2012 |

*Primary Examiner* — Marcia Watkins
(74) *Attorney, Agent, or Firm* — Noah J. Hayward (57) ABSTRACT

A prosthetic terminal device includes a wrist interface portion, a passive element and an active element. The passive element includes at least two finger-like projections extending from a base in a direction substantially away from the wrist interface portion. The passive element is fixed in relation to the wrist interface portion. The active element is configured to be positioned relative to the passive element and the wrist interface portion to achieve a plurality of grasp positions of the prosthetic terminal device based on one dimension of closure control of the active element in combination with a plurality of different fixable orientation positions of the active element. Each of the different fixable orientation positions is associated with at least one grasp position and at least one of the fixable orientation positions is associated with at least two grasp positions.

19 Claims, 10 Drawing Sheets

(56) References Cited

U.S. PATENT DOCUMENTS

| | | | |
|---|---|---|---|
| 2008/0188952 A1* | 8/2008 | Veatch et al. | 623/57 |
| 2009/0069942 A1 | 3/2009 | Takahashi | |
| 2010/0161130 A1 | 6/2010 | Kim et al. | |
| 2010/0179453 A1 | 7/2010 | Schweighofer et al. | |
| 2012/0150321 A1 | 6/2012 | Goldfarb et al. | |
| 2012/0165979 A1 | 6/2012 | Lim et al. | |

* cited by examiner

MULTIPLE GRASP PROSTHETIC TERMINAL DEVICE

CROSS-REFERENCE TO RELATED APPLICATIONS

This application claims priority to and the benefit of co-pending U.S. Provisional Application No. 61/593,523 filed on Feb. 1, 2012, the entire contents of which are hereby incorporated herein by reference.

TECHNICAL FIELD

Example embodiments generally relate to prosthetic devices and, more particularly, relate to a prosthetic terminal device that provides robust grasping capabilities within the context of a relatively simple structure.

BACKGROUND

Prosthetic devices have continued to evolve over time to improve the functional capabilities and aesthetic appearance of such devices. However, in many cases, improving the functional capabilities of prosthetic devices correspondingly increases both the complexity and the cost of the devices. For example, providing high functioning prosthetic terminal devices, or end effectors, that restore hand like capabilities may be possible via the use of multiple active and articulable finger-like projections. Complex control circuitry, and numerous motor operated articulated joints may be needed to provide such a high functioning prosthetic terminal device.

Although modern technology has advanced to the point where it is possible to develop extremely functional and lifelike prosthetic limbs, it may not be economically feasible to mass produce such limbs. Moreover, many individuals that need prosthetic devices may desire simpler and more cost effective alternatives.

BRIEF SUMMARY OF SOME EXAMPLES

Accordingly, some example embodiments may enable the provision of a relatively high functioning prosthetic device within the context of a relatively simple structure. In this regard, some example embodiments may provide a relatively simple structure including a passive portion and an active portion that is capable of being manipulated using a combination of manual and myoelectric controlled operations to orient the active portion relative to the passive portion for the achievement of a relatively high number of different grasping positions.

In one example embodiment, a prosthetic terminal device is provided. The prosthetic terminal device may include a wrist interface portion, a passive element and an active element. The passive element may include at least two finger-like projections extending from a base in a direction substantially away from the wrist interface portion. The passive element may be fixed in relation to the wrist interface portion. The active element may be configured to be positioned relative to the passive element and the wrist interface portion to achieve a plurality of grasp positions of the prosthetic terminal device based on one dimension of closure control of the active element in combination with a plurality of different fixable orientation positions of the active element. Each of the different fixable orientation positions may be associated with at least one grasp position and at least one of the fixable orientation positions is associated with at least two grasp positions.

BRIEF DESCRIPTION OF THE SEVERAL VIEWS OF THE DRAWING(S)

Having thus described example embodiments of the invention in general terms, reference will now be made to the accompanying drawings, which are not necessarily drawn to scale, and wherein:

DETAILED DESCRIPTION

Some example embodiments now will be described more fully hereinafter with reference to the accompanying drawings, in which some, but not all example embodiments are shown. Indeed, the examples described and pictured herein should not be construed as being limiting as to the scope, applicability or configuration of the present disclosure. Rather, these example embodiments are provided so that this disclosure will satisfy applicable legal requirements. Like reference numerals refer to like elements throughout.

Some example embodiments may enable a relatively simple structure to provide a relatively high functioning prosthetic terminal device (or end effector). Such a structure may employ a relatively small number of components and relatively simple control circuitry to accomplish the provision of a plurality of different grasp options using a combination of manual and automatic (or myoelectrically controlled) positioning adjustments.

Figure 1:
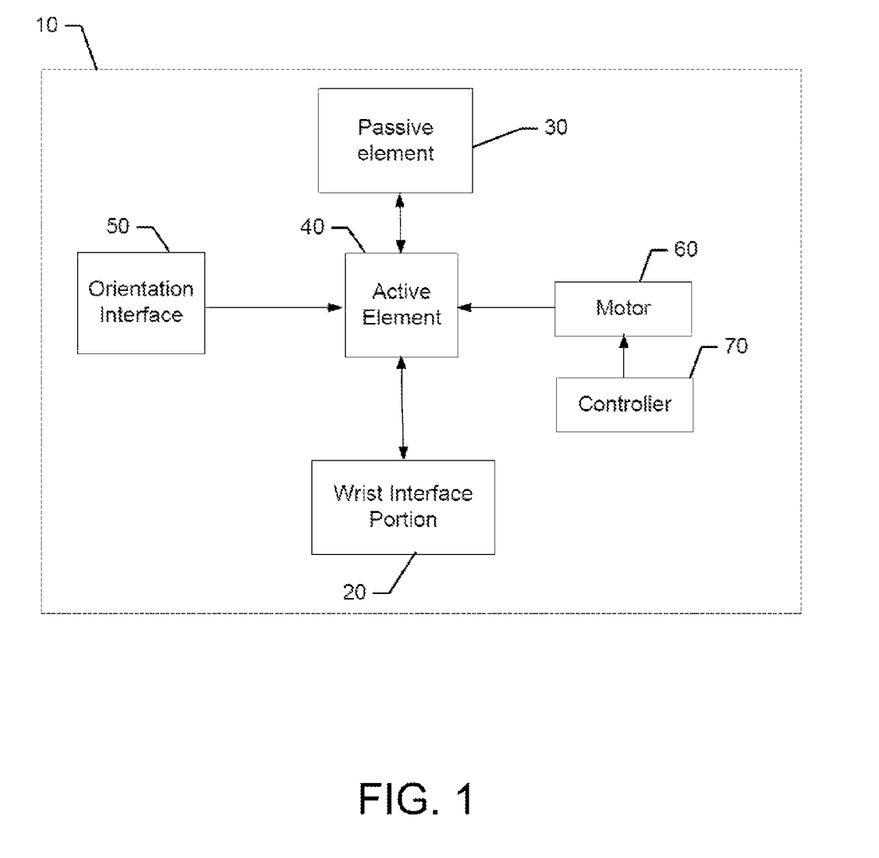
FIG. 1 is a functional block diagram of a terminal device according to an example embodiment.

An example embodiment will be described herein as it relates to a prosthetic terminal device that is designed to provide hand like capabilities to an amputee employing a combination of manual and myoelectric control. In this regard, FIG. 1 is a functional block diagram of a terminal device 10 according to an example embodiment. As shown in FIG. 1, the terminal device 10 may include a wrist interface portion 20 and a passive element 30 that may be fixed relative to the wrist interface portion 20. The terminal device 10 may also include an active element 40 that is repositionable relative to the passive element 30 in order to achieve different grasping positions. The active element 40 may include an orientation interface 50 that enables the orientation of the active element 40 to be changed relative to the passive element 30. In an example embodiment, the orientation interface 50 may be manually operable to enable the active element 40 to be rotated to one of a plurality of different fixed orientation positions. Each fixed orientation position may be associated with at least one grasping position and, in some cases, at least one of the orientation positions may be associated with at least two grasping positions.

In an example embodiment, the wearer of the terminal device 10 may use the wearer's other hand to manually reposition the orientation of the active element 40 via the orientation interface 50. However, in some cases, pressure may be exerted on the active element 40 via some other object in order to achieve operation of the orientation interface 50 to change the orientation of the active element 40. Once the active element 40 is rotated to a desired orientation position for the grasping position that is desired, the active element 40 may be actuated to achieve the desired grasping position. In an example embodiment, the terminal device 10 may further include a motor 60, which may be a battery operated, small electric motor. The motor 60 may drive movement of one or more articulated joints of the active element 40 to drive the active element 40 toward the passive element 30 to achieve the desired grasping position. Operation of the motor 60 may be controlled via a controller 70. In an example embodiment, the controller 70 may be a myoelectric controller. As such, the controller 70 may be configured to measure electromyogram (EMG) signals generated by muscles in a residual limb, and may control the motor 60 responsive to detection of the EMG signals.

In some embodiments, the controller 70 may include or otherwise be in communication with processing circuitry that is configurable to perform actions in accordance with example embodiments described herein. As such, for example, at least some of the functions attributable to the image controller 70 may be carried out by or otherwise instructed by the processing circuitry. The processing circuitry may therefore provide the hardware for hosting software to configure the system for manipulating closure of the active element 40 responsive to EMG signals consistent with example embodiments. The processing circuitry may be configured to perform function execution including closure control of the active element 40. In some embodiments, the processing circuitry may be embodied as a chip or chip set. In other words, the processing circuitry may comprise one or more physical packages (e.g., chips) including materials, components and/or wires on a structural assembly (e.g., a baseboard). In an example embodiment, the processing circuitry may include one or more instances of a processor and memory that may be in communication with or otherwise control the active element 40. As such, the processing circuitry may be embodied as a circuit chip (e.g., an integrated circuit chip) configured (e.g., with hardware, software or a combination of hardware and software) to perform operations described herein.

Figure 2A:
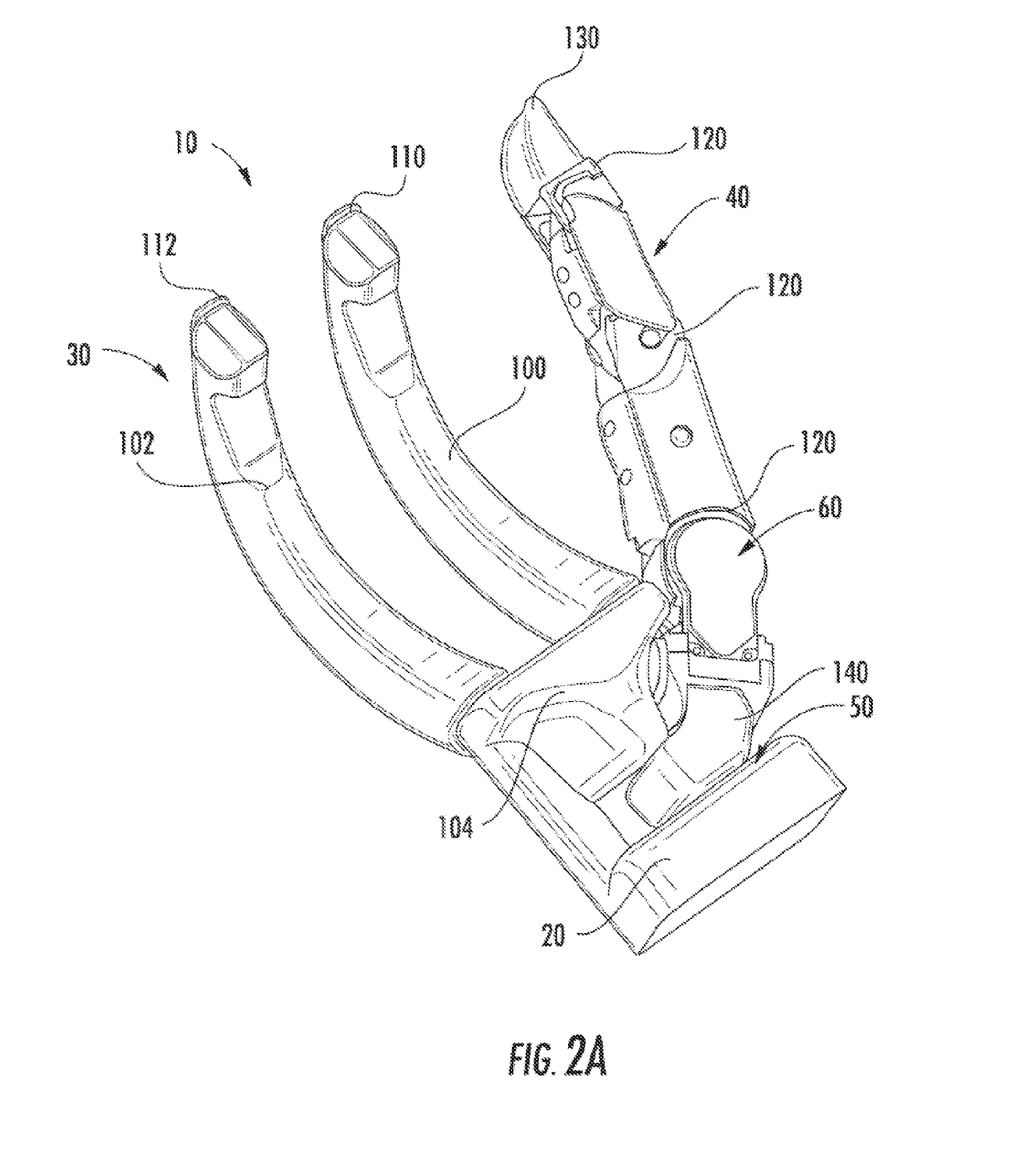
FIG. 2A is a perspective view of the terminal device according to an example embodiment.
Figure 2B:
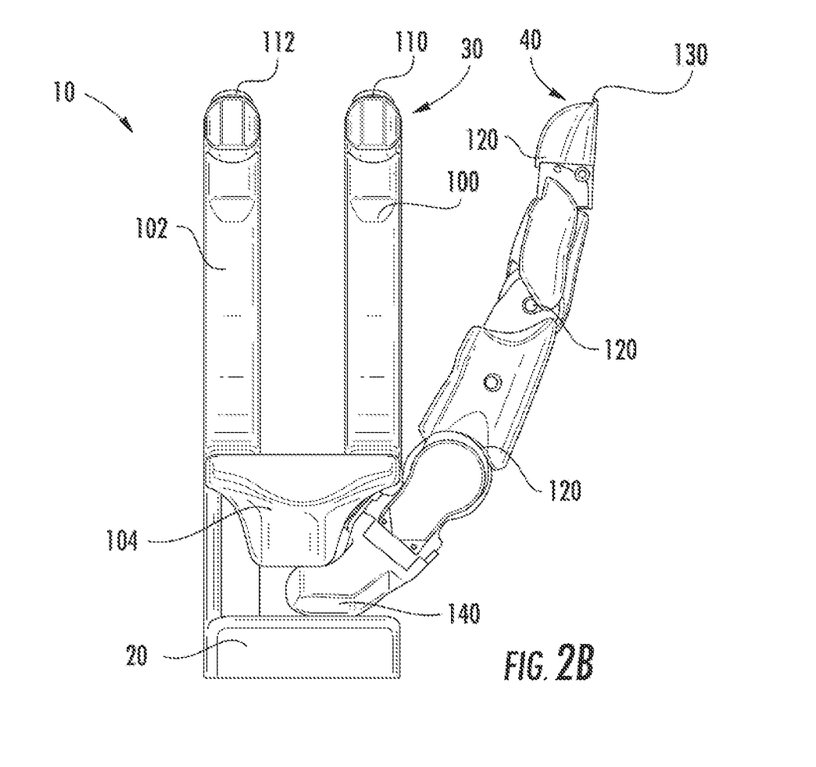
FIG. 2B illustrates a front view of the terminal device according to an example embodiment.
Figure 2C:
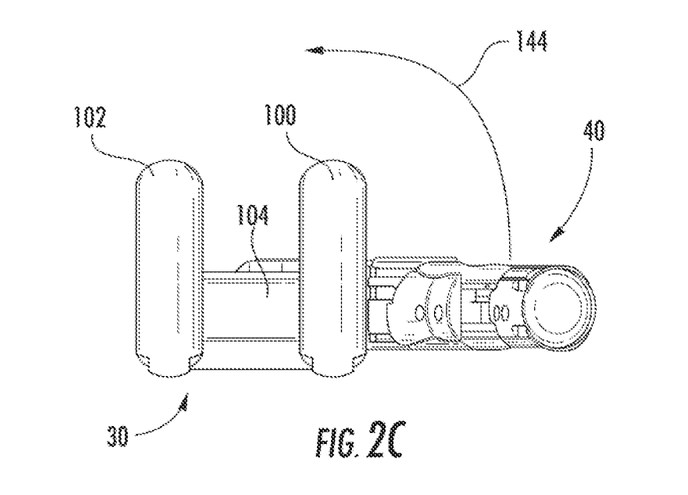
FIG. 2C illustrates a top view of the terminal device according to an example embodiment.

A discussion regarding the operation and structure of one example embodiment of the terminal device 10 will now be described in reference to FIG. 2, which includes FIGS. 2A, 2B and 2C. FIG. 2A is a perspective view of the terminal device 10 according to an example embodiment. FIG. 2B illustrates a front view of the terminal device 10 according to an example embodiment. FIG. 2C illustrates a top view of the terminal device according to an example embodiment. Referring now to FIG. 2, the passive element 30 may include two elongate members 100 and 102 that may extend from a base 104 that is fixed to the wrist interface portion 20. The elongate members 100 and 102 may separately extend away from the base 104 in substantially the same direction to terminate at respective distal ends 110 and 112. In an example embodiment, the elongate members 100 and 102 may each be curved, having substantially a C shape.

In some cases, the elongate members 100 and 102 may be made of a rigid material such as a metal, hard plastic or composite material. The elongate members 100 and 102 may be similar in size to a human finger and may be oriented in a curled position to form the C shape. In some embodiments, the elongate members 100 and 102 may extend substantially parallel to each other and may be spaced apart from each other by a distance that may be substantially equal to the width of each of the elongate members 100 and 102. However, in some cases, wider or narrower distances between the elongate members 100 and 102 may be provided.

In an example embodiment, the distal ends 110 and 112 may have grip features disposed thereon. The grip features may include protruding portions that may act like fingernails to facilitate the effectiveness of some grips. Additionally or alternatively, the grip features may be provided by the use of rubber or some at least partially compressible material that may provide a degree of compression in various ones of the grasp positions.

The active element 40 may include one or more articulated joints 120. Responsive to operation of the motor 60, the articulated joints 120 may be driven to cause the active element 40 to move closer to the passive element 30 (e.g., via contraction) or farther apart from the passive element 30 (e.g., via expansion). In this regard, for example, when the motor 60 causes the articulated joints 120 to contract, the active element 40 may move closer to the passive element 30. Meanwhile, when the motor 60 causes the articulated joints 120 to operate to elongate the active element 40 (i.e., expand), the active element 40 may move farther away from the passive element 30.

The active element 40 may further include a distal end 130 that may also include grip features similar to those described above. Thus, for example, dependent upon the orientation of the active element 40, when the active element 40 contracts, the distal end 130 of the active element 40 may approach a portion of the passive element 30 in some form of pincer movement. The specific orientation of the active element 40, and the corresponding portion of the passive element 30 that is approached during contraction of the articulated joints 120 will determine the grasp position that results from the movement.

In an example embodiment, the active element 40 may include a base portion 140 that is at an opposite end of the active element 40 relative to the distal end 130. The base portion 140 may be positioned to fit between the base 104 of the passive portion 30 and the wrist interface portion 20, which may connect to the amputated limb, or to a prosthetic arm that may be connected to the amputated limb. The base portion 140 may be configured to rotate about an axis that is substantially perpendicular to, and extends between, the surfaces of the base 104 and the wrist interface portion 20 that are proximate to the base portion 140. In some cases, the base portion may be enabled to rotate between a first rotational limit shown in FIG. 2C at which the active element 40 is oriented to be substantially in-line with a longitudinal length of the base 104 to a second rotational limit that may be at least 90 degrees in the direction shown by arrow 144. When rotated to the first rotational limit, the active element 40 may contract to drive the distal end 130 thereof toward a side portion of the elongate member 100. Meanwhile, when rotated to the second rotational limit, the active element 40 may contract to drive the distal end 130 thereof toward the distal end 112 of the elongate member 102.

As indicated above, the orientation interface 50 may be manually operable to enable the active element 40 to be rotated to one of a plurality of different fixed orientation positions. In an example embodiment, two of the different fixed positions may include the positions at the first and second rotational limits and at least one additional fixed position may be defined between the first and second rotational limits. Moreover, in one embodiment, there may be two fixed positions defined between the first and second rotational limits to define a total of four orientation positions to which the orientation interface 50 may be operated in order to define corresponding different relative orientations between the passive element 30 and the active element 40. However, the degree of contraction of the active element 40 at each orientation position (or at least at some of the orientation positions) may enable different grasp positions to be defined.

FIG. 3, which includes FIGS. 3A, 3B, 3C, 3D, 3E and 3F, defines six different grasp positions that are achievable using an example embodiment. The six different grasp positions of an example embodiment may include lateral grasp position, a first finger precision grasp position, a three jaw chuck grasp position, a cylindrical grasp position, a second finger precision grasp position, and a hook grasp position.

Figure 3A:
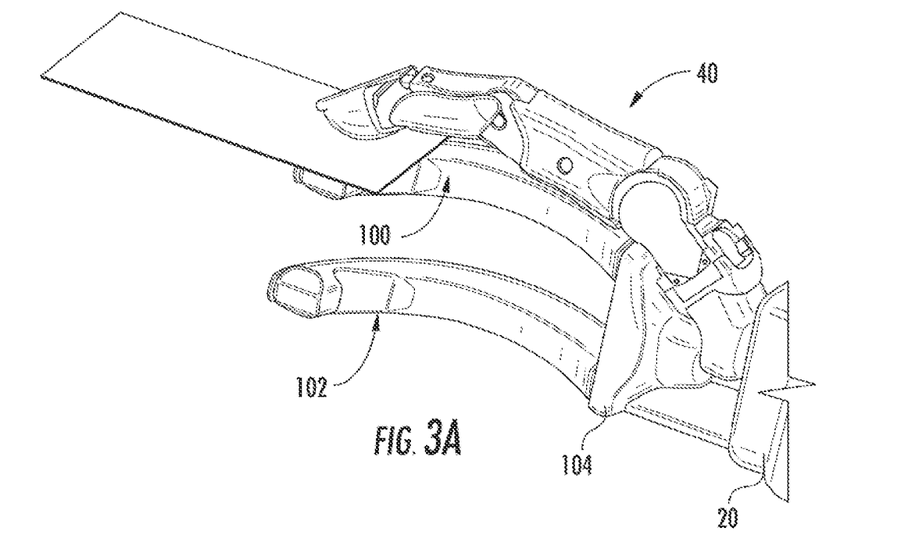
FIG. 3A illustrates the terminal device in a lateral grasp position according to an example embodiment.

In this regard, FIG. 3A illustrates the terminal device 10 in a lateral grasp position according to an example embodiment. In the lateral grasp position, which may alternatively be referred to as the key grasp position, the active element 40 is at the first rotational limit and the contraction of the active element 40 draws the distal end 130 thereof toward a side of the elongate member 100. Ultimately, contact may be provided between the distal end 130 and the side of the elongate member 100. This grasp position may approximate the grasp formed by moving the thumb into contact with a side of the first (or pointer) finger.

Figure 3B:
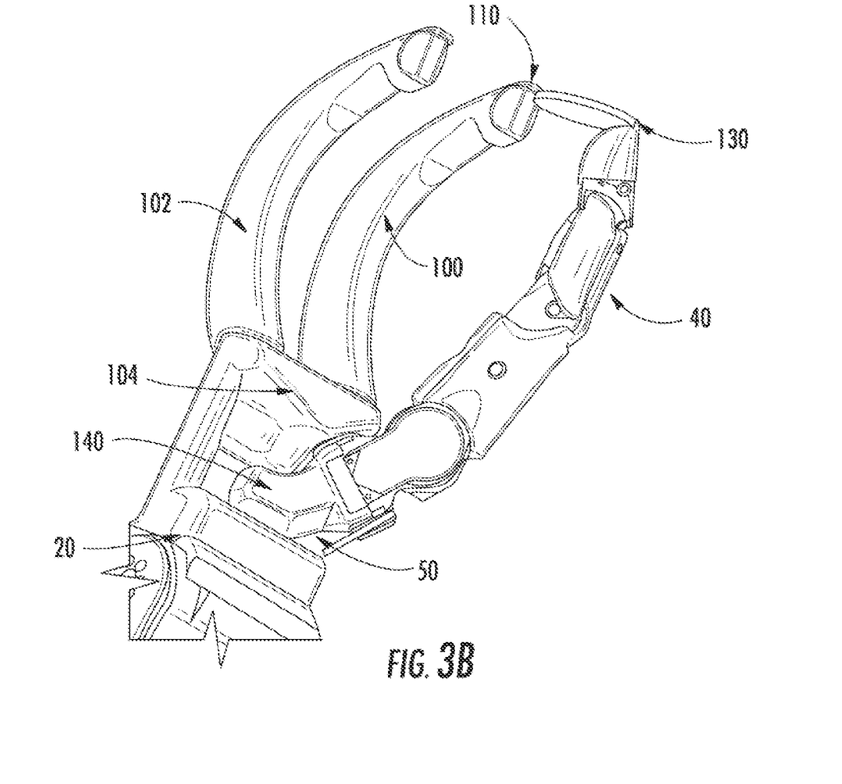
FIG. 3B illustrates the terminal device in a first finger precision grasp position according to an example embodiment.

FIG. 3B illustrates the terminal device 10 in a first finger precision grasp position according to an example embodiment. In the first finger precision grasp position, the active element 40 is at a first interior fixed rotation position that is between the first rotational limit and the second rotational limit (but closer to the first rotational limit). Contraction of the active element 40 draws the distal end 130 thereof toward the distal end 110 of the elongate member 100. Ultimately, contact may be provided between the distal ends 130 and 110. This grasp position may approximate the grasp formed by moving the thumb into contact with a tip of the first (or pointer) finger.

Figure 3C:
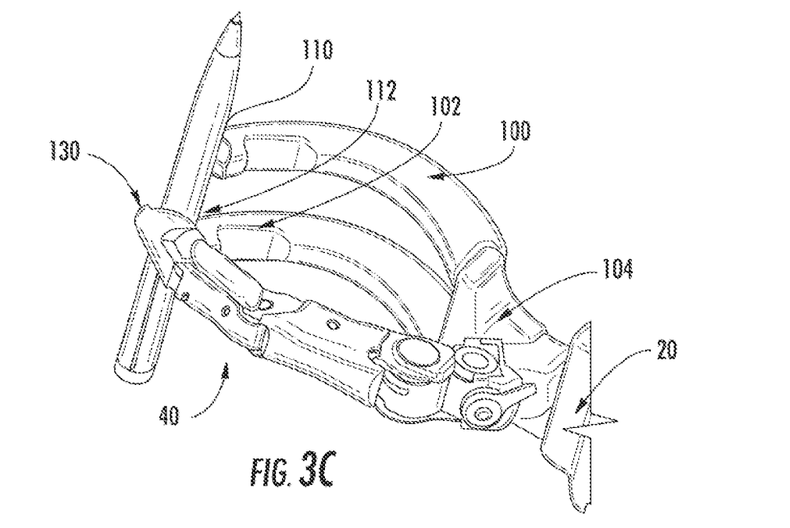
FIG. 3C illustrates the terminal device in a three jaw chuck grasp position according to an example embodiment.

FIG. 3C illustrates the terminal device in a three jaw chuck grasp position according to an example embodiment. In the three jaw chuck grasp position, the active element 40 is at a second interior fixed rotation position that is between the first rotational limit and the second rotational limit (but closer to the second rotational limit). Contraction of the active element 40 draws the distal end 130 toward a point substantially between the distal ends 110 and 112 of the elongate members 100 and 102. Ultimately, the distal end 130 may be provided between the distal ends 110 and 112. However, if an object is grasped, the object will prevent the distal end 130 from advancing to the point between the distal ends 110 and 112. This grasp position may approximate the grasp formed by moving the thumb into contact with an object that is held between the tip of the thumb and tips of the first (or pointer) finger and the second (or middle) finger.

Figure 3D:
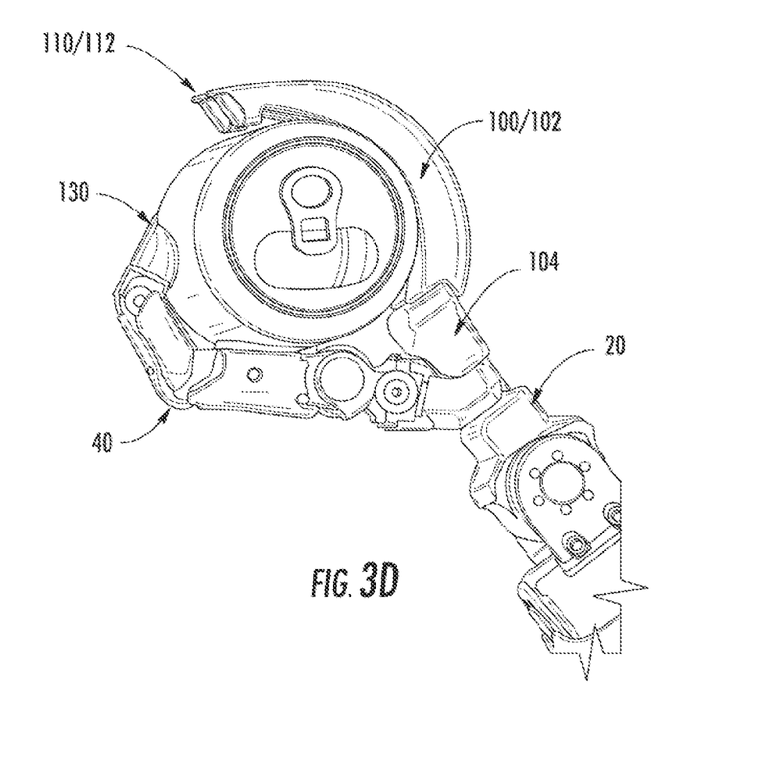
FIG. 3D illustrates the terminal device in a cylindrical grasp position according to an example embodiment.

FIG. 3D illustrates the terminal device 10 in a cylindrical grasp position according to an example embodiment. In the cylindrical grasp position, the active element 40 may be at the second interior fixed rotation position that is between the first rotational limit and the second rotational limit (but closer to the second rotational limit). Contraction of the active element 40 draws the distal end 130 toward a point substantially between the distal ends 110 and 112 of the elongate members 100 and 102. An object may be placed within the curve of the elongate members 100 and 102 so that the elongate members 100 and 102 and the active element 40 substantially wrap around the sides of the object as shown in FIG. 3D However, if an object is grasped, the object will prevent the distal end 130 from advancing to the point between the distal ends 110 and 112. This grasp may approximate the grasp formed by moving the thumb into contact with an object that is held between the tip of the thumb and tips of the first (or pointer) finger and the second (or middle) finger.

Figure 3E:
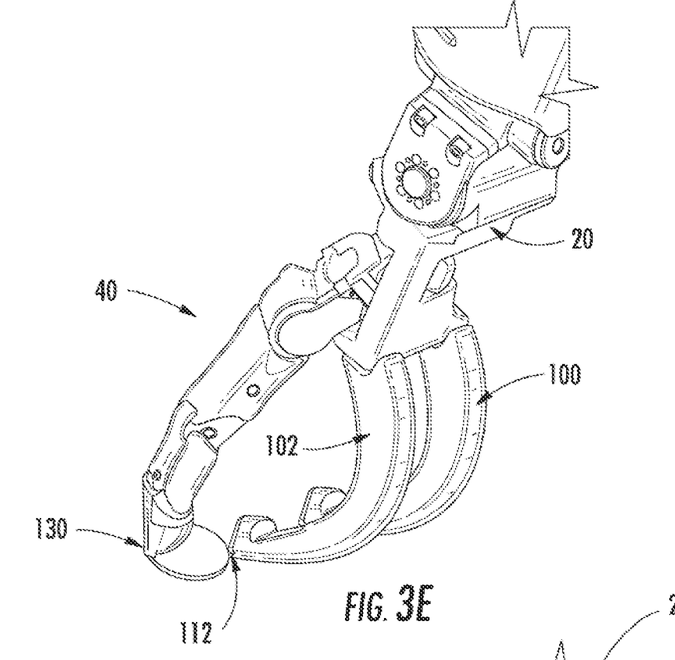
FIG. 3E illustrates the terminal device in a second finger precision grasp position according to an example embodiment.

FIG. 3E illustrates the terminal device 10 in a second finger precision grasp position according to an example embodiment. In the second finger precision grasp position, the active element 40 is at the second rotational limit. Contraction of the active element 40 draws the distal end 130 thereof toward the distal end 112 of the elongate member 102. Ultimately, contact may be provided between the distal ends 130 and 112. This grasp position may approximate the grasp formed by moving the thumb into contact with a tip of the second (or middle) finger.

Figure 3F:
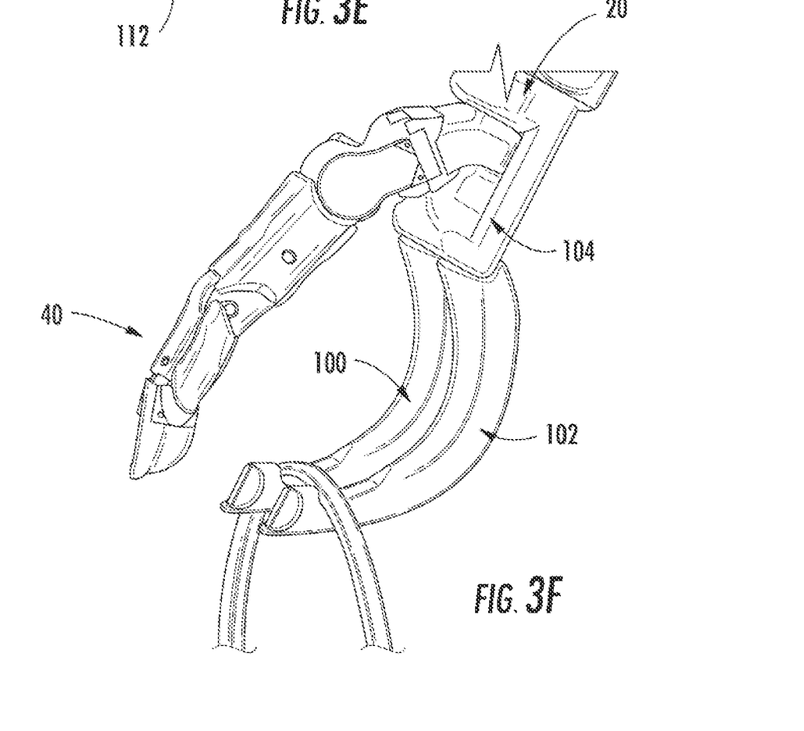
FIG. 3F illustrates the terminal device in a hook grasp position according to an example embodiment.

FIG. 3F illustrates the terminal device 10 in a hook grasp position according to an example embodiment. In the hook grasp position, the active element 40 may be positioned at the second rotational limit, or at either of the first and second interior fixed rotation positions, but the active element 40 may not be contracted. This grasp position may approximate the grasp formed when an object, strap or other implement that can be lifted by hooking the object instead of grasping it with a pincer movement is held via extending the first and second fingers to hold the object.

Figure 4A:
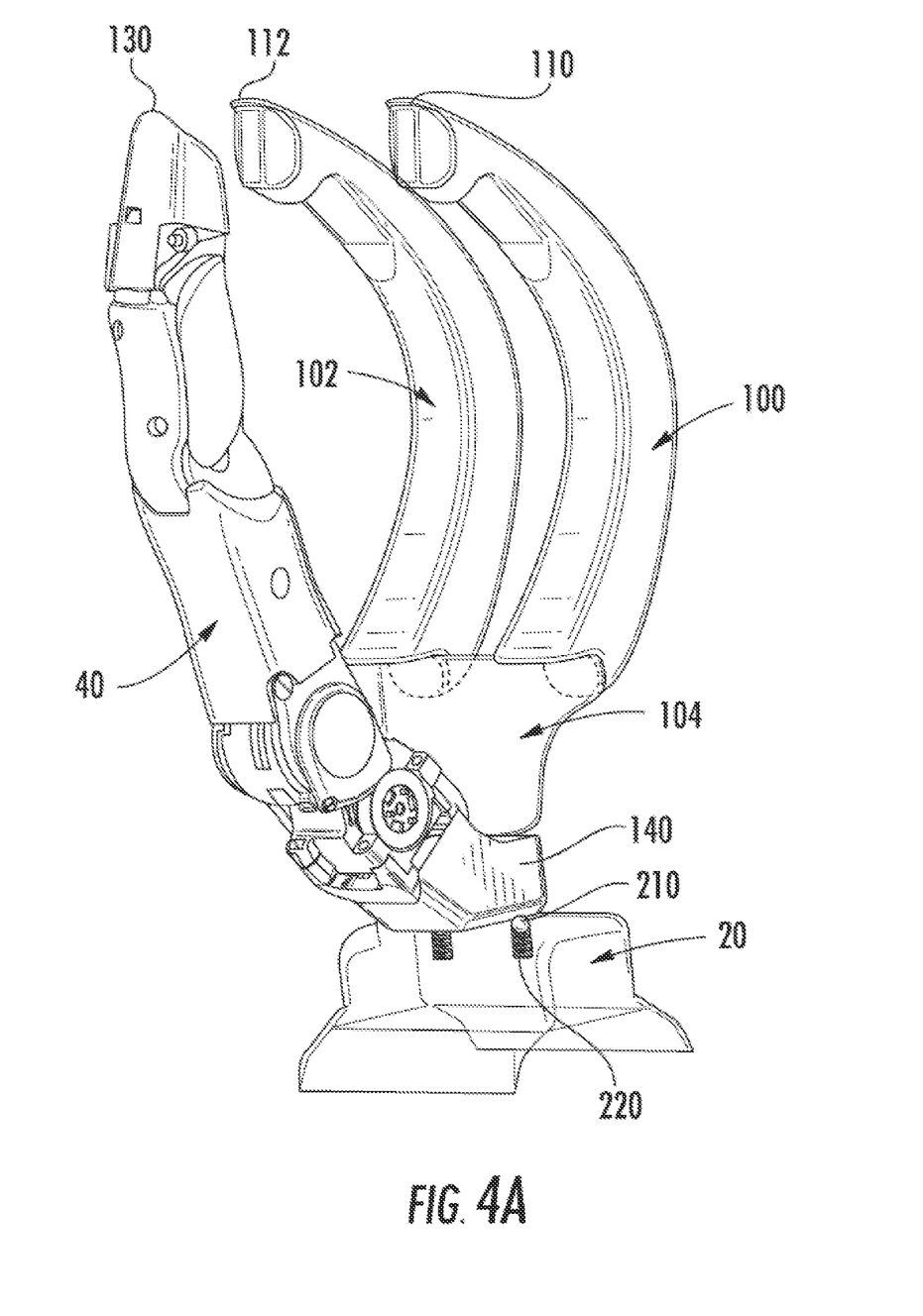
FIG. 4A illustrates a perspective view of the terminal device with a palm body portion partially cutaway to expose active orientation components according to an example embodiment.
Figure 4B:
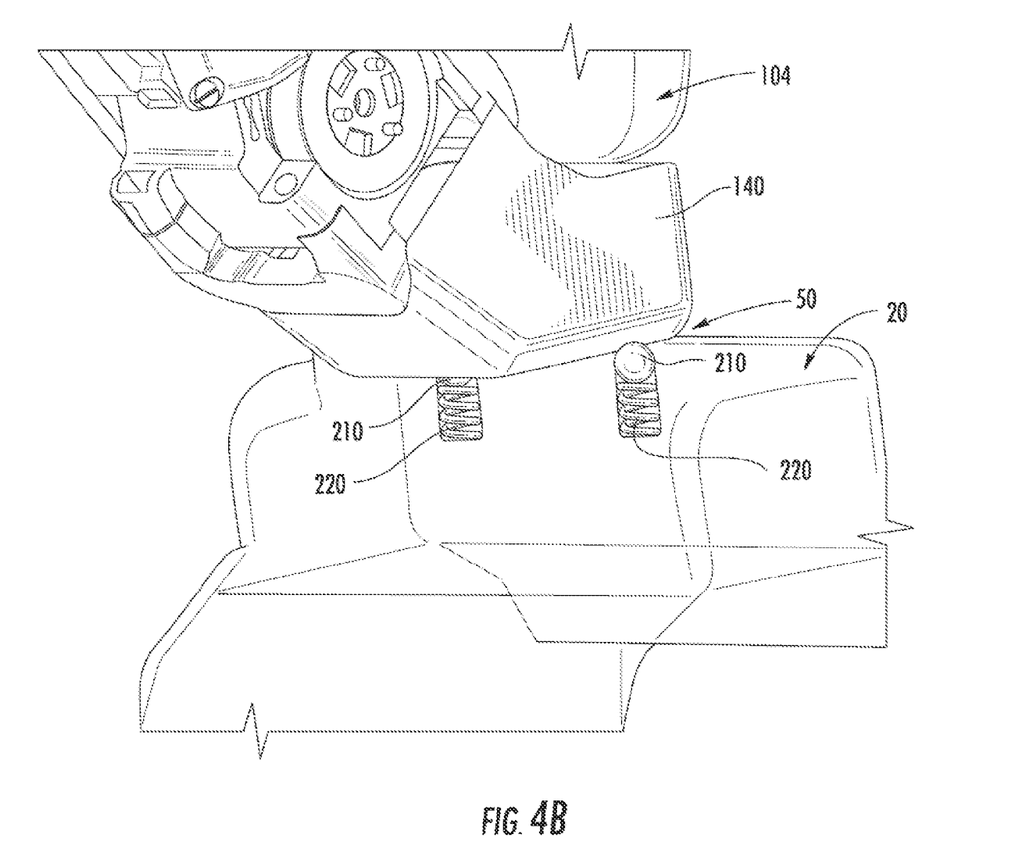
FIG. 4B illustrates a perspective view of the palm body portion of FIG. 4A according to an example embodiment.
Figure 5A:
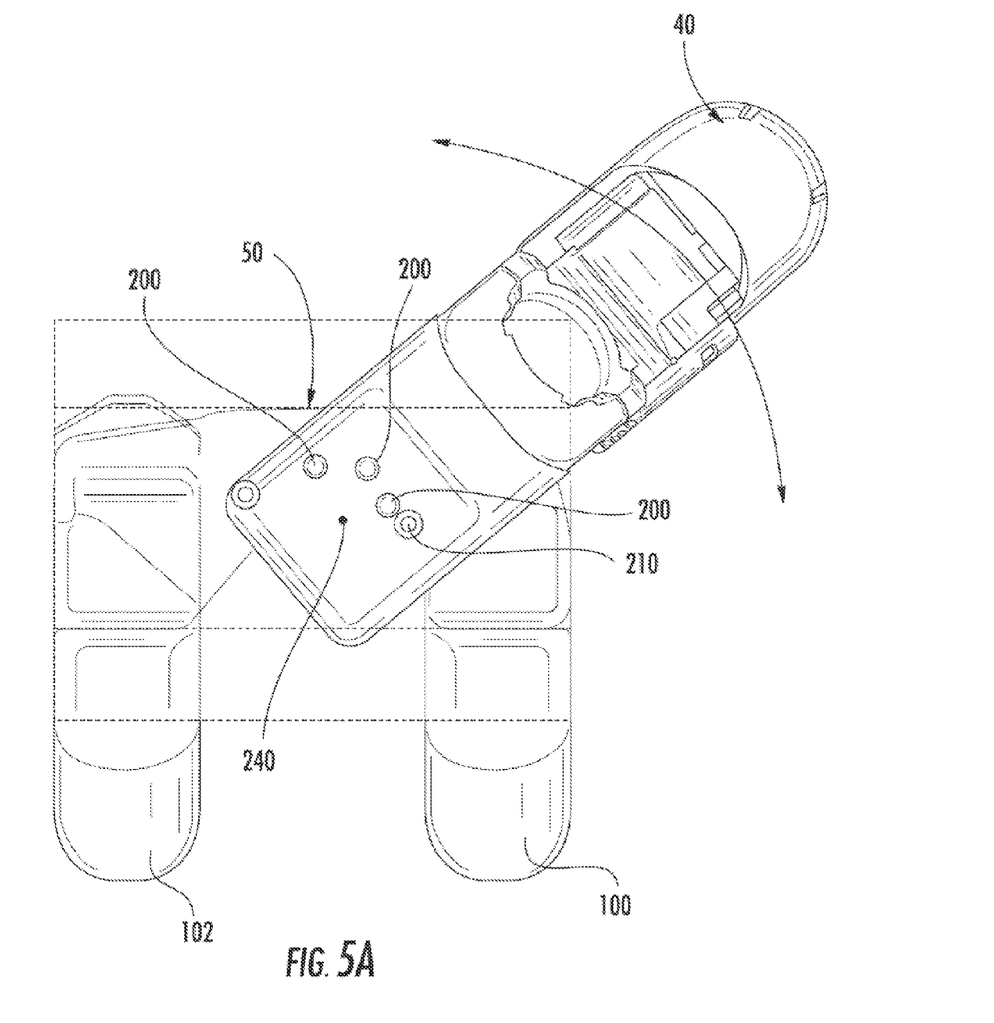
FIG. 5A illustrates an underside view of an interface between the palm body portion and the active member in one rotational orientation according to an example embodiment.

The orientation positions that are achievable according to an example embodiment are provided via relatively easily releasable position locks that are incorporated into the orientation interface 50. FIGS. 4 and 5, which include FIGS. 4A and 4B and FIGS. 5A and 5B, respectively, illustrate views of the terminal device 10 that are aimed to facilitate explanation of the orientation interface 50. In this regard, FIG. 4A illustrates a perspective view of the terminal device with a palm body portion partially cutaway to expose active orientation components according to an example embodiment, while FIG. 4B illustrates a closer perspective view of the palm body portion of FIG. 4A according to an example embodiment. FIG. 5A illustrates an underside view of an interface between the palm body portion and the active member in one rotational orientation according to an example embodiment, and FIG. 5B illustrates the underside view of the interface between the palm body portion and the active member in another rotational orientation according to an example embodiment.

Figure 5B:
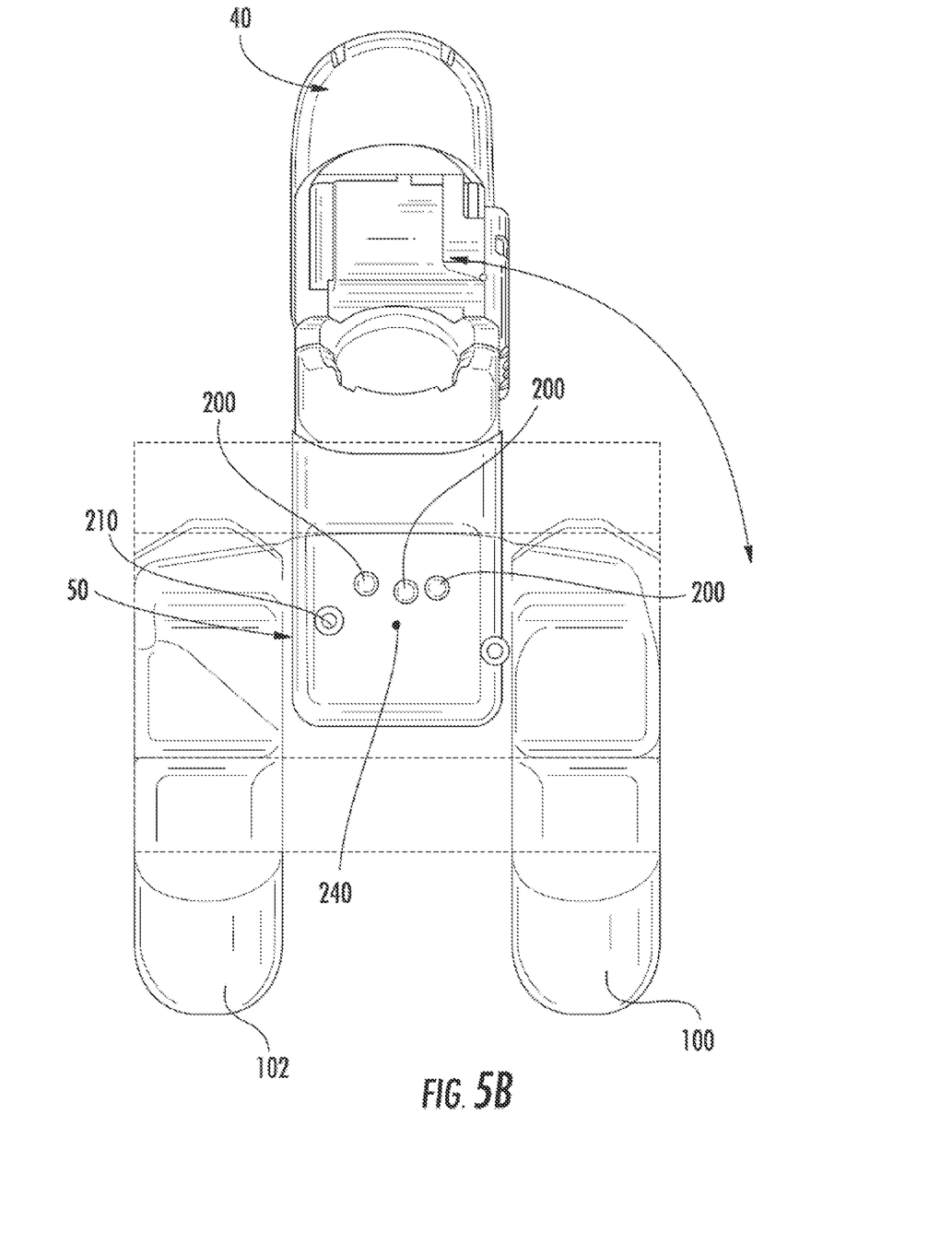
FIG. 5B illustrates the underside view of the interface between the palm body portion and the active member in another rotational orientation according to an example embodiment.

As shown in FIGS. 4 and 5, the orientation positions incorporated into the orientation interface 50 may be provided by releasable position locks that may be formed in any suitable manner. In an example embodiment, the base portion 140 may include a plurality of captive relief areas 200 that are configured to receive locking elements 210 that are biased toward insertion in the relief areas 200 by a compliant element 220 that is associated with each respective locking element 210. The locking elements 210 may be disposed at a surface of the wrist interface portion 20 that faces the base portion 140. The compliant elements 220 may be disposed in recesses in the wrist interface portion 20 to force the locking elements 210 toward the base portion 140

As indicated above, the active member 40 may be rotatable between the various orientation positions by rotating about a rotation point 240 (or axis of rotation). In an example embodiment, two locking elements 210 may be provided at different locations relative to the rotation point 240. For example, each of the locking elements 210 may be a different distance from the rotation point 240 and/or each of the locking elements 210 may be at a different direction from the rotation point 240. Meanwhile, the captive relief areas 200 may be disposed to be on the surface of the base portion 140 at portions of a contact surface defined between the base portion 140 and the wrist interface portion 20 so that the captive relief areas 200 can receive a respective one of the locking elements 210 when aligned therewith. Accordingly, the captive relief areas 200 may also be disposed different distances and orientations from the rotation point 240 so that the locking element 210 that is a first distance away from the rotation point 240 may engage one of the captive relief areas 200 that is also the first distance away from the rotation point 240 when they are aligned. Meanwhile, the locking element 210 that is a second distance away from the rotation point 240 may engage one of the captive relief areas 200 that is also the second distance away from the rotation point 240 when they are aligned.

The captive relief areas 200 may be hemispherical reliefs or cutouts formed in the surface of the base portion 140 and the locking elements 210 may be balls or spheres of similar diameter to the diameter of the hemispherical reliefs. The balls or spheres may be made of metal, rigid plastics or composite materials. However, other mechanisms, materials and/or shapes may be employed in alternative embodiments. In some cases, the compliant elements 220 may be helical springs that are biased to exert a force tending to push the locking elements 210 away from the wrist interface portion 20. However, it should be appreciated that other types of springs or other materials that can be utilized as biasing members may be employed in alternative embodiments.

Accordingly, example embodiments may be provided to increase the utility of a prosthetic terminal device by providing a relatively simple and inexpensive structure that may be made to provide a plurality of different grasp positions. Such a prosthetic terminal device may include a wrist interface portion, a passive element and an active element. The passive element may include at least two finger-like projections extending from a base in a direction substantially away from the wrist interface portion. The passive element may be fixed in relation to the wrist interface portion. The active element may be configured to be positioned relative to the passive element and the wrist interface portion to achieve a plurality of grasp positions of the prosthetic terminal device based on one dimension of closure control of the active element in combination with a plurality of different fixable orientation positions of the active element. Each of the different fixable orientation positions may be associated with at least one grasp position and at least one of the fixable orientation positions is associated with at least two grasp positions.

In some embodiments, the different fixable orientation positions may be achieved through manual rotation of the active element about a rotation axis defined between the passive element and the wrist interface portion. In such an example, the rotation axis may extend substantially perpendicular to opposing faces of the passive element and the wrist interface portion. In some cases, the prosthetic terminal device may further include an orientation interface that includes at least one locking element configured to engage a corresponding one of a plurality of captive relief areas. Each captive relief area may correspond to a respective one of the different fixable orientation positions. In this regard, the captive relief areas may be defined as hemispherical cutouts in an otherwise substantially planar surface, and the at least one locking element may be a spherical structure biased toward insertion in a hemispherical cutout that is aligned therewith. In some cases, the hemispherical cutouts may be disposed on a surface of the active element that faces the wrist interface, and the at least one locking element may be biased toward the hemispherical cutouts from a corresponding at least one recess formed in a surface of the wrist interface portion that faces the active element. In an example embodiment, the at least one locking element may be biased toward the captive relief areas by a compliant element disposed at the wrist interface portion. In some embodiments, the compliant element may be embodied as a helical spring disposed in a recess formed in a surface of the wrist interface portion that faces the active element. In some examples, the orientation interface may include at least two locking elements and each of the at least two locking elements may be disposed a different distance from an axis of rotation of the active element. At least one of the captive relief areas may be disposed at each respective different distance from the axis of rotation of the active element to enable alignment between the at least one of the captive relief areas disposed at each respective different distance from the axis of rotation and a corresponding one of the at least two locking elements when the active element is rotated about the axis of rotation to place the corresponding one of the at least two locking elements in alignment with a respective one of the captive relief areas.

In an example embodiment, the one dimension of closure control may be provided via movement of the active element toward or away from the passive element in a current one of the different fixable positions to define a respective one of the grasp positions. In such an example, the one dimension of closure control may be provided based on application of a control signal to a motor controlling movement of articulated segments of the active element for contraction of the active element or expansion of the active element. In some cases, a base portion of the active element may rotate about the axis of rotation between a first rotational limit at which the active element is oriented to be substantially in-line with a longitudinal length of the base of the passive element and a second rotational limit at which the active element is rotated at least 90 degrees about the axis of rotation relative to the first rotational limit. In some embodiments, at least one additional fixed position may be defined between the first and second rotational limits. In an example embodiment, four different fixable orientation positions may be attainable to define six different grasp positions including a lateral grasp position, a first finger precision grasp position, a three jaw chuck grasp position, a cylindrical grasp position, a second finger precision grasp position, and a hook grasp position. However, it should be appreciated that alternative example embodiments may provide more or fewer fixable orientation positions to obtain more or fewer corresponding grasp positions. The active element may be positionable to the first rotational limit and the active element is contracted toward a side of a first one of the passive elements to define the lateral grasp position. The active element may be positionable to the second rotational limit and the active element is contracted toward a distal end of a second one of the passive elements to define the second finger precision grasp position. The active element may be positionable to the at least one additional fixed position between the first and second rotational limits to define the first finger precision grasp position, the three jaw chuck grasp position, the cylindrical grasp position, and the hook grasp position. In some cases, the passive elements are curved as they extend away from the base toward respective distal ends thereof. In some embodiments, a distal end of at least one of the passive elements or the active element includes grip features.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Moreover, although the foregoing descriptions and the associated drawings describe exemplary embodiments in the context of certain exemplary combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. In cases where advantages, benefits or solutions to problems are described herein, it should be appreciated that such advantages, benefits and/or solutions may be applicable to some example embodiments, but not necessarily all example embodiments. Thus, any advantages, benefits or solutions described herein should not be thought of as being critical, required or essential to all embodiments or to that which is claimed herein. Although specific terms are employed herein, they are used in a generic and descriptive sense only and not for purposes of limitation.

What is claimed is:

1. A prosthetic terminal device comprising:
    a wrist interface portion;
    a passive element including at least two finger-like projections, each of the at least two finger-like projections extending from a base in a direction substantially away from the wrist interface portion and terminating in a distal end having a grip feature, the passive element including the at least two finger-like projections being fixed in relation to the wrist interface portion; and
    an active element configured to be positioned relative to the passive element and the wrist interface portion to achieve a plurality of grasp positions of the prosthetic terminal device based on one dimension of closure control of the active element in combination with a plurality of different fixable orientation positions of the active element,
    wherein each of the different fixable orientation positions is associated with at least one grasp position and at least one of the fixable orientation positions is associated with at least two grasp positions, and
    wherein a base portion of the active element rotates about an axis of rotation between a first rotational limit at which the active element is oriented to be substantially in-line with a longitudinal length of the base of the passive element and a second rotational limit at which the active element is rotated at least 90 degrees about the axis of rotation relative to the first rotational limit.

2. The prosthetic terminal device of claim 1, wherein the different fixable orientation positions are achieved through manual rotation of the active element about the rotation axis defined between the passive element and the wrist interface portion.

3. The prosthetic terminal device of claim 2, wherein the rotation axis extends substantially perpendicular to opposing faces of the passive element and the wrist interface portion.

4. The prosthetic terminal device of claim 1, further comprising an orientation interface, the orientation interface including at least one locking element configured to engage a corresponding one of a plurality of captive relief areas, each captive relief area corresponding to a respective one of the different fixable orientation positions.

5. The prosthetic terminal device of claim 4, wherein the at least one locking element is biased toward the captive relief areas by a compliant element disposed at the wrist interface portion.

6. The prosthetic terminal device of claim 5, wherein the compliant element comprises a helical spring disposed in a recess formed in a surface of the wrist interface portion that faces the active element.

7. The prosthetic terminal device of claim 1, wherein the one dimension of closure control is provided via movement of the active element toward or away from the passive element in a current one of the different fixable positions to define a respective one of the grasp positions.

8. The prosthetic terminal device of claim 7, wherein the one dimension of closure control is provided based on application of a control signal to a motor controlling movement of articulated segments of the active element for contraction of the active element or expansion of the active element.

9. The prosthetic terminal device of claim 1, wherein at least one additional fixed position is defined between the first and second rotational limits.

10. The prosthetic terminal device of claim 9, wherein four different fixable orientation positions are attainable to define six different grasp positions including a lateral grasp position, a first finger precision grasp position, a three jaw chuck grasp position, a cylindrical grasp position, a second finger precision grasp position, and a hook grasp position.

11. The prosthetic terminal device of claim 10, wherein the active element is positionable to the first rotational limit and the active element is contracted toward a side of a first one of the passive elements to define the lateral grasp position.

12. The prosthetic terminal device of claim 10, wherein the active element is positionable to the second rotational limit and the active element is contracted toward a distal end of a second one of the passive elements to define the second finger precision grasp position.

13. The prosthetic terminal device of claim 10, wherein the active element is positionable to the at least one additional fixed position between the first and second rotational limits to define the first finger precision grasp position, the three jaw chuck grasp position, the cylindrical grasp position, and the hook grasp position.

14. The prosthetic terminal device of claim 1, wherein the passive elements are curved as they extend away from the base toward respective distal ends thereof.

15. The prosthetic terminal device of claim 1, wherein a distal end of the passive element or the active element includes grip features.

16. A prosthetic terminal device comprising:
    a wrist interface portion;
    a passive element including at least two finger-like projections, each of the at least two finger-like projections extending from a base in a direction substantially away from the wrist interface portion and terminating in a distal end having a grip feature, the passive element including the at least two finger-like projections being fixed in relation to the wrist interface portion; and an active element configured to be positioned relative to the passive element and the wrist interface portion to achieve a plurality of grasp positions of the prosthetic terminal device based on one dimension of closure control of the active element in combination with a plurality of different fixable orientation positions of the active element, and an orientation interface, the orientation interface including at least one locking element configured to engage a corresponding one of a plurality of captive relief areas, each captive relief area corresponding to a respective one of the different fixable orientation positions, wherein each of the different fixable orientation positions is associated with at least one grasp position and at least one of the fixable orientation positions is associated with at least two grasp positions, and wherein the captive relief areas are defined as hemispherical cutouts in an otherwise substantially planar surface, and wherein the at least one locking element is a spherical structure biased toward insertion in a hemispherical cutout that is aligned therewith.

17. The prosthetic terminal device of claim 16, wherein the hemispherical cutouts are disposed on a surface of the active element that faces the wrist interface, and wherein the at least one locking element is biased toward the hemispherical cutouts from a corresponding at least one recess formed in a surface of the wrist interface portion that faces the active element.

18. A prosthetic terminal device comprising:
a wrist interface portion;
a passive element including at least two finger-like projections extending from a base in a direction substantially away from the wrist interface portion, the passive element being fixed in relation to the wrist interface portion;

an active element configured to be positioned relative to the passive element and the wrist interface portion to achieve a plurality of grasp positions of the prosthetic terminal device based on one dimension of closure control of the active element in combination with a plurality of different fixable orientation positions of the active element; and an orientation interface including at least one locking element configured to engage a corresponding one of a plurality of captive relief areas, each captive relief area corresponding to a respective one of the different fixable orientation positions, wherein each of the different fixable orientation positions is associated with at least one grasp position and at least one of the fixable orientation positions is associated with at least two grasp positions, and wherein the orientation interface includes at least two locking elements and wherein each of the at least two locking elements is disposed a different distance from an axis of rotation of the active element.

19. The prosthetic terminal device of claim 18, wherein at least one of the captive relief areas is disposed at each respective different distance from the axis of rotation of the active element to enable alignment between the at least one of the captive relief areas disposed at each respective different distance from the axis of rotation and a corresponding one of the at least two locking elements when the active element is rotated about the axis of rotation to place the corresponding one of the at least two locking elements in alignment with a respective one of the captive relief areas.

* * * * *